(12) United States Patent
Liao et al.

(10) Patent No.: US 9,189,851 B2
(45) Date of Patent: Nov. 17, 2015

(54) METHOD OF MOTION COMPENSATION FOR TRANS-CATHETER AORTIC VALVE IMPLANTATION

(75) Inventors: Rui Liao, Princeton Junction, NJ (US); Ali Kamen, Princeton, NJ (US); Matthias John, Nürnberg (DE); Alois Nöttling, Pottenstein (DE); Jan Boese, Eckental (DE); Marily Sarmiento, New York, NY (US)

(73) Assignees: SIEMENS AKTIENGESELLSCHAFT, München (DE); SIEMENS MEDICAL SOLUTIONS USA, INC., Malvern, PA (US)

( * ) Notice: Subject to any disclaimer, the term of this patent is extended or adjusted under 35 U.S.C. 154(b) by 838 days.

(21) Appl. No.: 12/984,954

(22) Filed: Jan. 5, 2011

(65) Prior Publication Data
US 2011/0164035 A1 Jul. 7, 2011

Related U.S. Application Data

(60) Provisional application No. 61/292,892, filed on Jan. 7, 2010.

(51) Int. Cl.
*G06T 15/00* (2011.01)
*G06T 7/00* (2006.01)
*G06T 7/20* (2006.01)

(52) U.S. Cl.
CPC .............. *G06T 7/0024* (2013.01); *G06T 7/0028* (2013.01); *G06T 7/2033* (2013.01); *G06T 2207/10072* (2013.01); *G06T 2207/10121* (2013.01); *G06T 2207/10124* (2013.01); *G06T 2207/30048* (2013.01); *G06T 2207/30101* (2013.01)

(58) Field of Classification Search
CPC ............... A61B 2019/5238; A61B 2019/5265; A61B 5/06; A61B 6/032
USPC ......................................................... 345/419
See application file for complete search history.

(56) References Cited

U.S. PATENT DOCUMENTS

| 2008/0177280 A1* | 7/2008 | Adler et al. .................... 606/130 |
| 2010/0056919 A1* | 3/2010 | Abe .............................. 600/443 |
| 2010/0191102 A1* | 7/2010 | Steinberg et al. ............. 600/424 |

OTHER PUBLICATIONS

Holger Timinger, Sascha Krueger, Klaus Dietmayer, and Joern Borgert, entitled, "Motion Compensated Coronary Interventional Navigation by Means of Diaphram Tracking and Elastic Motion Models", Physics in Medicine and Biology, 2005, pp. 491-503, vol. 50 (No. 3).

Selen Atasoya, Martin Grohera, Darko Zikica, Ben Glockera, Tobias Waggershauserb (MD), Marcus Pfisterc and Nassir Navaba, entitled, "Real-time Respiratory Motion Tracking: Roadmap Correction for Hepatic Artery Catheterizations", Proceedings of Society of Photo-Optical Instrumentation Engineers (SPIE) Medical Imaging 2008, p. 691815 vol. 6918, San Diego, CA USA.

(Continued)

*Primary Examiner* — Phi Hoang
*Assistant Examiner* — Mohammad H Akhavannik

(57) ABSTRACT

A method (10) to compensate for cardiac and respiratory motion in cardiac imaging during minimal invasive (e.g., trans-catheter) AVI procedures by image-based tracking (20, 25) on fluoroscopic images.

27 Claims, 3 Drawing Sheets

(56) References Cited

OTHER PUBLICATIONS

Alexander Brost, Rui Liao, Joachim Hornegger and Norbert Strobel, entitled, "3-D Respiratory Motion Compensation during EP Procedures by Image-Based 3-D Lasso Catheter Model Generation and Tracking", Medical Image Computing and Computer-Assisted Intervention—MICCAI 2009, Lecture Notes in Computer Science, Sep. 2009, pp. 394-401, vol. 5761, London UK.

Hari Sundar, Ali Khamene, Liron Yatziv and Chenyang Xu, entitled, "Automatic Image-Based Cardiac and Respiratory Cycle Synchronization and Gating of Image Sequences", Medical Image Computing and Computer-Assisted Intervention—MICCAI 2009, Lecture Notes in Computer Science, 2009, p. 381, vol. 5762.

* cited by examiner

METHOD OF MOTION COMPENSATION FOR TRANS-CATHETER AORTIC VALVE IMPLANTATION

CROSS-REFERENCE TO RELATED APPLICATIONS

This application claims the benefit of Provisional U.S. Patent Application Ser. No. 61/292,892, entitled, "Motion Compensation for Trans-Catheter Aortic Valve Implantation by Image-Based Tracking on Fluoroscopy", filed in the name of Rui Liao, Ali Kamen, Matthias John, Alois Noettling, Jan Boese, and Marily Sarmiento, on Jan. 7, 2010, the disclosure of which is also hereby incorporated herein by reference.

FIELD OF INVENTION

The present invention relates to cardiac imaging. More particularly, the present invention relates to respiratory motion compensation in certain cardiac imaging.

BACKGROUND OF THE INVENTION

Aortic valve disease (such as regurgitation or stenosis) affects over 100 million people globally, with half of them requiring implantation of a mechanical or biological aortic valve to replace the diseased valve. In 2007, there were about seventy to eighty thousand aortic valve implantation (AVI) procedures in the United States, and there is a steady growth trend. Traditionally, an AVI procedure is a complex open-heart surgical procedure. However, in recent years, the trans-catheter approach has rapidly emerged as a minimal invasive alternative for AVI procedures. In minimal invasive AVI procedures, a prosthetic valve is inserted into a patient's heart via a catheter. Intra-operative 2D X-ray imaging is used for monitoring the procedure and positioning the valve. Unfortunately, 2D X-ray projection images generally cannot distinguish soft tissue. To address this issue, image integration combining a high-resolution 3D aortic volume (which may be reconstructed from a preparatory, pre-operative imaging scan using one of the various imaging modalities, such as CT, MR, C-Arm CT, etc.) with the 2D fluoroscopic images has been developed (i.e., fluoroscopic overlay image guidance). The projection of the 3D aortic volume onto the frames of the fluoroscopy image sequence establishes a single image coordinate system and permits clearer visualization for navigating the catheter, positioning the valve and, otherwise, monitoring the procedure.

The 3D aortic volume used for the overlay is acquired either at a given cardiac and respiratory phase or during fast pacing. Consequently, the current fluoroscopic overlay techniques are usually static. In other words, the techniques do not follow the heart while the heart beats and moves through the breathing cycle. This results in apparent displacements of the static aortic volume due to cardiac motions (movement of the heart due to the cardiac cycle) and respiratory motions (respiratory-induced movement of the heart). Cardiac motion could be compensated at least partly using ECG gating, which are techniques in which image acquisition is triggered by a start pulse derived from an ECG taken from the patient during imaging.

However, breathing motion is less periodic than cardiac motion and needs to be explicitly compensated to provide for more accurate navigation. To accomplish this, a fluoroscopic overlay technique needs to generate a dynamic overlay. Motion-compensated navigation for coronary intervention was suggested in an article by Holger Timinger, Sascha Krueger, Klaus Dietmayer And Joern Borgert, entitled, "Motion Compensated Coronary Interventional Navigation by Means of Diaphram Tracking and Elastic Motion Models", Physics in Medicine and Biology 2005, pp 491-503, Vol. 50 (No. 3). However, the proposed method is based on a magnetic tracking system for device localization using specialized catheters and, therefore, is more expensive compared to image-based localization. Image-based device localization for breathing motion compensation during hepatic artery catheterization and electrophysiology was shown in two recent articles (one article is by Selen Atasoya, Martin Grohera, Darko Zikica, Ben Glockera, Tobias Waggershauserb (MD), Marcus Pfisterc and Nassir Navaba, entitled, "Real-time Respiratory Motion Tracking: Roadmap Correction for Hepatic Artery Catheterizations", Proceedings of Society of Photo-Optical Instrumentation Engineers (SPIE) Medical Imaging 2008, p. 691815, Vol. 6918, San Diego, Calif. USA and the other article is by Alexander Brost, Rui Liao, Joachim Hornegger and Norbert Strobel, entitled, "3-D Respiratory Motion Compensation during EP Procedures by Image-Based 3-D Lasso Catheter Model Generation and Tracking", Medical Image Computing and Computer-Assisted Intervention—MICCAI 2009, Lecture Notes in Computer Science, September 2009, pp. 394-401, Vol. 5761).

There is a need for image-based localization for both cardiac and respiratory motion compensation during minimal invasive AVI procedures. There is also a need for such techniques that do not utilize specialized catheters and control systems.

SUMMARY OF THE INVENTION

The present invention obviates the aforementioned problems by providing a method of motion compensation in cardiac imaging using a dynamic overlay of a 3D aortic volume with an intra-operative fluoroscopic image sequence of a target cardiac region, comprising estimating the motion of the target cardiac region by tracking an image object throughout the image sequence and adjusting the 3D aortic volume in the overlay with the fluoroscopic image sequence using the estimated motion of the target cardiac region. The image object may comprise calcifications at the targeted cardiac region, or a pigtail catheter at the targeted cardiac region that injects contrast agent for the fluoroscopy imaging. The image object may also comprise an image object that, in the imaging plane, moves infrequently relative to the target cardiac region; moves due to cardiac and respiratory motion; and moves with the targeted cardiac region motion, or an image object that, in the imaging plane, moves infrequently with respect to the target cardiac region; moves due to cardiac and respiratory motion; and moves in a correlated manner with the targeted cardiac region motion that may be described by a correlation motion model and wherein the adjusting step comprises adjusting the 3D aortic volume in the overlay with the fluoroscopic image sequence using the estimated motion of the target cardiac region and the correlation motion model. The cardiac imaging may be conducted during a trans-catheter aortic valve implantation (AVI) procedure and the target cardiac region comprises the aortic root. The fluoroscopic image sequence of a target cardiac region may comprise a biplane fluoroscopic image sequence; the estimating step may comprise estimating either or both translational and rigid-body transformation of the target cardiac region by tracking the image object in 3D against the two views of a biplane fluoroscopic image sequence; and the adjusting step may comprise adjusting the 3D aortic volume in the 3D space using the estimated transformation.

The present invention also provides a method for compensating for motion in cardiac imaging, comprising overlaying a 3D aortic volume of a patient with a first frame of a fluoroscopic image sequence of a target cardiac region; detecting a calcification at the target cardiac region; tracking the calcification on a subsequent frame of the image sequence and obtaining the corresponding estimated 2D motion vector; and moving the 3D aortic volume in the imaging plane using the estimated 2D motion vector. The overlaying step may further comprise confirming the accuracy of the overlay of the 3D aortic volume using a contrast agent injection. The detecting step may be accomplished by the imaging system automatically or with manual interaction. Also, the detecting step may comprise automatically detecting the calcification on the 3D aortic volume; projecting the detected calcification onto the 2D projection plane using the known geometry; and detecting the calcification on the fluoroscopic image sequence using the projection as the initial position followed by a local search of dark objects around the neighborhood.

The method may further comprise determining if the tracked calcification is not sufficiently close to the target cardiac region to represent the global motion of the target cardiac region; building a correlation motion model between the motion of the tracked calcification and the motion of the target cardiac region; and moving the 3D aortic volume in the imaging plane using the estimated 2D motion vector and the correlation motion model. The building step may comprise placing a pigtail catheter of the contrast agent injector temporarily stationary at the target cardiac region; tracking in 2D simultaneously the pigtail catheter and the calcification; and correlating the motion at the pigtail catheter with the motion estimated at the tracked calcification. Alternatively, the building step may comprise obtaining the motion at the target cardiac region by injecting contrast agent and tracking the opacified target cardiac region or may comprise obtaining the motion at the target cardiac region by a non-image based localization method. Further, the building step may comprise building a correlation motion model between the motion of the tracked calcification and the motion of the target cardiac region separately for each cardiac phase.

The cardiac imaging may be conducted during a trans-catheter aortic valve implantation (AVI) procedure and the target cardiac region comprises the aortic root. In such case, the detecting step may comprise detecting a calcification at either or both the aortic root and the proximal end of the coronary arteries.

The present invention also provides a method of 3D motion estimation and compensation in cardiac imaging comprising building a 3D respiratory motion trajectory for each cardiac phase of the patient from two monoplane fluoroscopic image sequences acquired during free breathing; overlaying a 3D aortic volume of a patient with a first frame of a fluoroscopic image sequence of a target cardiac region; detecting a calcification in the target cardiac region; tracking the calcification on a subsequent frame of the image sequence and obtaining an estimated 3D motion vector by intersecting the back-projection ray from the tracked calcification with the respiratory motion trajectory for the current cardiac phase; and moving the 3D aortic volume in 3D using the estimated 3D motion vector.

The present invention also provides another method for compensating for motion in cardiac imaging, comprising overlaying a 3D aortic volume of a patient with both views of a first frame of a biplane fluoroscopic image sequence of a target cardiac region; detecting on both views the pigtail catheter of the contrast agent injector at the target cardiac region; reconstructing the pigtail catheter in 3D; tracking the 3D pigtail catheter so the projection of the 3D pigtail catheter overlays best with the pigtail catheters in the two views of a subsequent frame and obtaining the corresponding estimated translational and/or rigid-body transformation; and moving the 3D aortic volume in the 3D space using the estimated translational and/or rigid-body transformation. The overlaying step may further comprise confirming the accuracy of an overlay of the 3D aortic volume with both views using a contrast agent injection. The detecting step may be accomplished by the imaging system automatically or with manual interaction. The reconstructing step may comprise reconstructing the pigtail catheter in 3D from the two pigtail catheter biplane projections. The cardiac imaging may be conducted during a trans-catheter aortic valve implantation (AVI) procedure and the target cardiac region comprises the aortic root.

The method may further comprise building a correlation motion model between the motions at different parts of the aorta; and moving the 3D aortic volume in the 3D space using the estimated translational and/or rigid-body transformation and the correlation motion model. The building step may then comprise placing the pigtail catheter of the contrast agent injector temporarily at the target cardiac region; and 3D tracking of the pigtail catheter. The building step may also comprise isolating cardiac motion and building a respiratory motion model.

The present invention provides another method for compensating for motion in cardiac imaging, comprising generating a layered digitally reconstructed radiograph (DRR) from a segmented 3D aortic volume of a patient; performing intensity-based 2D-3D registration between the 3D aortic volume and a 2D fluoroscopic image sequence of a target cardiac region to match the layered DRR against the X-ray projection of a frame of the image sequence; and adjusting the placement of a representation of the 3D aortic volume in the fluoroscopic imaging plane using the results of the layered 2D-3D registration. The method may further comprise segmenting the regions of the 3D aortic volume based on differing motion patterns or alignments among the regions. The cardiac imaging may be conducted during a trans-catheter aortic valve implantation (AVI) procedure and the target cardiac region comprises the aortic root.

The method may further comprise transforming the segmented 3D aortic volume, prior to generating a layered DRR, by performing either a rigid or affine transformation for each 3D region segmented from the 3D aortic volume in accordance with the following: $DRR_i = P(^iCT(T_i))$, where $DRR_i$ is a generated digitally reconstructed radiograph for the $i^{th}$ segmented part; P is the projection for generating a $DRR_i$ image; and $T_i$ is a different transformation for each respective $i^{th}$ segmented part. In such case, the generating step may comprise generating a DRR for each segmented region of the volume and accumulating all the DRRs to obtain a layered DRR. In addition, the performing step may match the layered DRR with the X-ray projection of a frame of the image sequence in accordance with the following: $\{T_i\} = \arg\max S(P(^iCT(T_i)), Xray)$, where S is a similarity measure comparing the DRRs and the X-ray projection images.

Advantageously, the present invention provides cardiac imaging that compensates for cardiac and breathing motion in both 2D and 3D imaging contexts. Methods carried out according to the present invention provide learning the motion model of the patient in both 2D and 3D and, when the 3D motion model is learned, the respective method can facilitate motion compensation for any working angles. Further, the methods utilize commonly available landmarks (for example, a pigtail catheter or calcium deposits) during AVI procedures for motion compensation, without a requirement for additional markers to be implanted into patients. Also, the methods utilize image-based tracking on fluoroscopic images for motion compensation, which is workflow-friendly and cost-effective. The methods do not require contrast agent administration and can be fully automatic without user interaction, for both monoplane and biplane systems.

DESCRIPTION OF THE DRAWINGS

For a better understanding of the present invention, reference is made to the following description of an exemplary embodiment thereof, and to the accompanying drawings, wherein.

DETAILED DESCRIPTION

Figure 1:
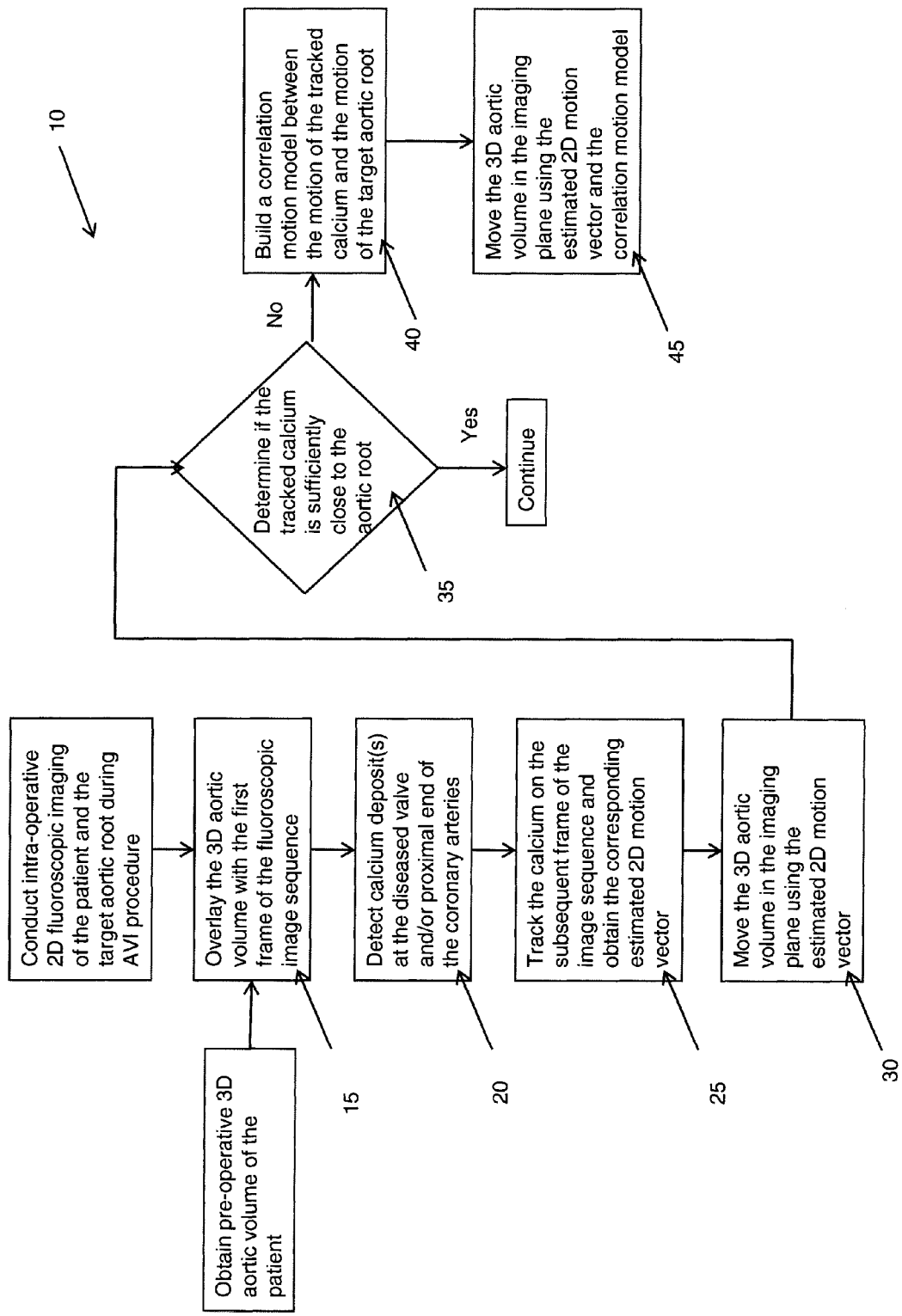
FIG. 1 is a flow chart of a first method to compensate for cardiac and respiratory motion for cardiac imaging carried out in accordance with the present invention.

The present invention provides several methods to compensate for cardiac and respiratory motion for cardiac imaging. The methods are particularly directed to compensate for cardiac and respiratory motion during minimal invasive (e.g., trans-catheter) AVI procedures by image-based tracking on fluoroscopic images. The methods are implemented with the assistance of the imaging system and its visualization and computing capabilities. As noted above, minimal invasive AVI procedures, like other complex non-invasive cardiac interventional procedures, are routinely guided by an X-ray coronary angiography system. Generally, a medical professional inserts an appropriate catheter into a blood vessel of the subject patient and advances the catheter to the target site (i.e., the aortic root, which is the outflow tract from the left ventricle to the aorta) to perform the desired interventional actions. To assist in the visualization for the AVI procedure, the medical professional utilizes the imaging system to retrieve and overlay a 3D aortic volume, reconstructed from a preparatory, pre-operative imaging scan of the patient, on the intra-operative 2D X-ray fluoroscopy images.

To generate a dynamic fluoroscopic overlay that compensates for motion, the methods of the present invention utilize commonly available landmarks or features in the images for tracking the motion of the target site. One such landmark or feature is the pigtail catheter which is routinely used in AVI procedures for injecting the contrast agent for the fluoroscopy imaging and which is typically placed at the aortic root. Another such landmark or feature, especially for AVI patients, is the accompanying calcifications (i.e., hardened depositions of calcium salts) at the diseased valve and/or the proximal end of the coronary arteries. The pigtail catheter and the calcium deposits represent suitable objects to be tracked in order to estimate the motion of the targeted area of AVI procedures, i.e., the aortic root. It is noted that the deformation (nonrigid-body motion) of the aortic root caused by cardiac motion is assumed to be negligible from the overlay, and therefore does not need to be compensated separately for the purpose of generating an adequate dynamic overlay.

Although there are few discernable features in typical fluoroscopy images during AVI procedures, other objects may also be used and incorporated into the framework if they possess the following properties:

a) they are at a relatively fixed position and are not frequently moved with respect to the aortic root during the procedure, b) their motion comes mainly from cardiac and respiratory motion, and c) their movement due to cardiac and respiratory motion either closely represents or is in a synchronized fashion with the global motion of the aortic root (i.e. the target for motion compensation during AVI procedures). In the latter case, a correlation model between the motion at the tracked object and the motion at the aortic root needs to be further developed (as described below).

FIG. 1 shows a first method 10 to compensate for cardiac and respiratory motion during minimal invasive (e.g., transcatheter) AVI procedures in accordance with the present invention. Specifically, the method 10 tracks a patient's calcium deposits on fluoroscopic images taken in a monoplane fluoroscopy system for motion estimation and compensation of the aortic root. The type of fluoroscopy system may be a monoplane or a biplane system. A monoplane system is less expensive and therefore more widely used than a biplane system. For a monoplane system, the combined motion from cardiac and respiration can be estimated and subsequently compensated accurately only in the 2D imaging plane. Nevertheless, for AVI procedures, 2D motion compensation in the dynamic overlay is considered to be largely sufficient for navigation and valve deployment purposes. 3D motion estimation and compensation on a monoplane system is possible if a proper correlation motion model can be built beforehand. For a biplane system, two synchronized biplane views are available all the time. Consequently, the underlying 3D motion can be estimated reliably by 3D tracking, leading to accurate and straightforward motion compensation in 3D.

The method 10 provides overlaying the 3D aortic volume with the first frame of a fluoroscopic image sequence, either manually or automatically (Step 15). The alignment or registration of the two may be confirmed by contrast injection. In Step 20, the calcium deposit(s) at the diseased valve and/or the proximal end of the coronary arteries is detected and then marked on the first frame using an appropriate graphical user interface (e.g. by drawing a rectangle containing the calcium or delineating the border of the calcium using polygons). The calcium may be detected automatically on the first frame via image-based localization methods. Automatic calcium detection may be further facilitated with the availability of the 3D volume as follows: automatically detecting the calcium on the 3D volume, projecting the detected calcium onto the 2D projection plane using the known geometry, and detecting the calcium on the fluoroscopy using the projection as the initial position followed by a local search of dark objects around the neighborhood.

In Step 25, the method 10 provides tracking the calcium on the subsequent frame of the image sequence automatically and obtaining the corresponding estimated 2D motion vector from a comparison of the two locations of the calcium. The calcium may be detected in the same or similar manner as described in the previous step. In Step 30, the 3D aortic volume is moved correspondingly in the imaging plane using the 2D motion vector estimated in the previous step. The method 10 may include a step (Step 35) to determine if the tracked calcium is not sufficiently close to the aortic root (e.g. at the more distal part of the coronary artery) and, therefore, does not closely represent the global motion of the aortic root. In such case, the method 10 provides building a correlation motion model between the motion at the tracked calcium and the motion at the target (i.e. aortic root) (Step 40). This can be achieved, for example, by putting the pigtail catheter temporarily stationary in the aortic root, tracking in 2D simultaneously the pigtail catheter and the calcium, and correlating the motion of the pigtail catheter with the motion estimated at the calcium. In this case, the method 10 then moves the 3D volume correspondingly in the imaging plane using the estimated 2D motion vector and the developed correlation motion model (Step 45). If the tracked calcium does closely represent the global motion of the aortic root, then only the estimated 2D motion vector is needed.

When building the correlation motion model, the motion at the aortic root may also be obtained by injecting contrast agent followed by tracking the opacified aortic root or by non-image based localization methods, e.g. via electromagnetic tracking. For better accuracy, the correlation motion model could be built separately for each cardiac phase. In such case, the cardiac phase may be obtained via ECG gating or image-based localization methods (this is described more fully in an article by Hari Sundar, Ali Khamene, Liron Yatziv and Chenyang Xu, entitled, "Automatic Image-Based Cardiac and Respiratory Cycle Synchronization and Gating of Image Sequences", Medical Image Computing and Computer-Assisted Intervention—MICCAI 2009, Lecture Notes in Computer Science, 2009, pp. 381-388, Vol. 5762). The correlation motion model may include an AR (auto-regressive) model, a state-space model, a neuronetwork, etc.

It is noted that 3D motion estimation and compensation on a monoplane system may be achieved by a) building 3D respiratory motion trajectory for each cardiac phase from two monoplane fluoroscopic image sequences acquired during free breathing; b) intersecting the backprojection ray from the tracked calcium with the respiratory motion trajectory for the current cardiac phase and obtaining the 3D motion vector; and c) moving the 3D aortic volume in 3D using the estimated 3D motion vector.

Figure 2:
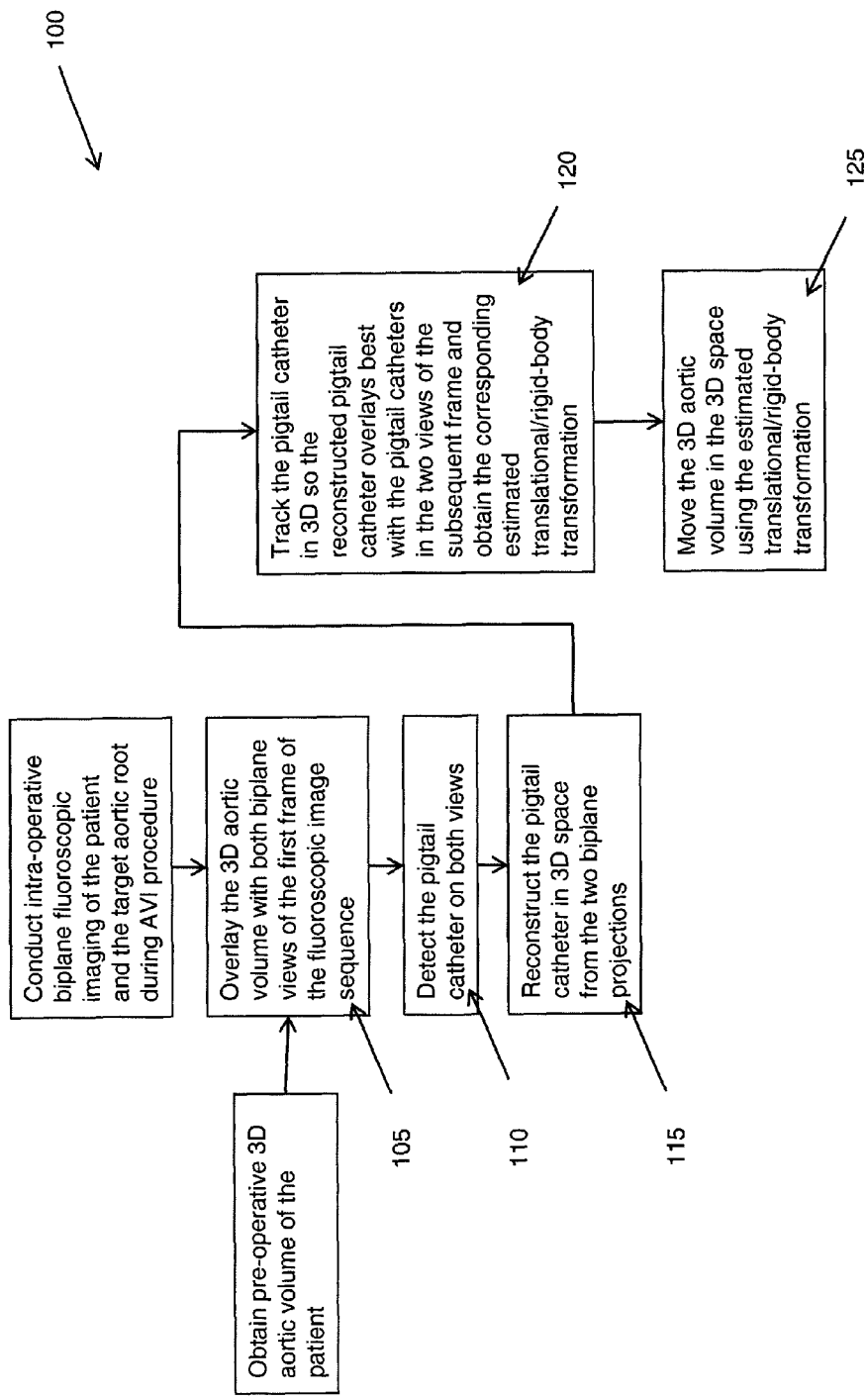
FIG. 2 is a flow chart of a second method to compensate for cardiac and respiratory motion for cardiac imaging carried out in accordance with the present invention.

FIG. 2 shows an alternative method 100 to compensate for cardiac and respiratory motion during minimal invasive (e.g., trans-catheter) AVI procedures in accordance with the present invention. The method 100 tracks the pigtail catheter on fluoroscopic images taken in a biplane fluoroscopy system for motion estimation and compensation of the aortic root. As with the first method 10, it is noted that the type of fluoroscopy system may be a biplane or monoplane system.

The method 100 provides overlaying the 3D aortic volume with both biplane views of the first frame of the fluoroscopy image sequence, either manually or automatically (Step 105). The alignment or registration needs to be accurate in the 3D physical space and may be confirmed by contrast injection under a biplane system. In Step 110, the pigtail catheter on both views for the first frame are detected, automatically or with manual interaction. In Step 115, the method 100 reconstructs the pigtail catheter in 3D from the two 2D pigtail catheter projections extracted in the previous step. The pigtail catheter may also be reconstructed using scanning provided by a DynaCT® angiographic imaging system by Siemens. The pigtail catheter in 3D is then tracked so that the projection of the tracked 3D catheter overlays best with the moving pigtail catheters shown in the two biplane fluoroscopic views in the subsequent frame (Step 120). In Step 125, the method 100 provides moving the 3D volume correspondingly in the 3D space using the translational (three degree translation) and/or rigid-body transformation (six degree translation and rotation) estimated in the previous Step 120.

The method 100 may also provide and utilize a correlation motion model. 3D motion can be learned for various parts of the aorta by 3D tracking of the pigtail catheter temporarily put at the target position (i.e. aortic root). The 3D motion estimated from tracking can be a combination of cardiac and breathing motion, and is further parameterized to provide an independent model for cardiac and breathing motion. An alternative is to isolate cardiac motion by ECG gating and build a breathing motion model from the ECG gated tracking. The correlation motion model can also be learned for the relationship between the motions at different parts of the aorta at different cardiac and breathing phases to provide quantitative analysis about the influence of breathing and cardiac motion on the anatomical change of the aorta. The cardiac and respiratory phase can be obtained via a surrogate signal such as an ECG and spirometer, or an image-based method.

Figure 3:
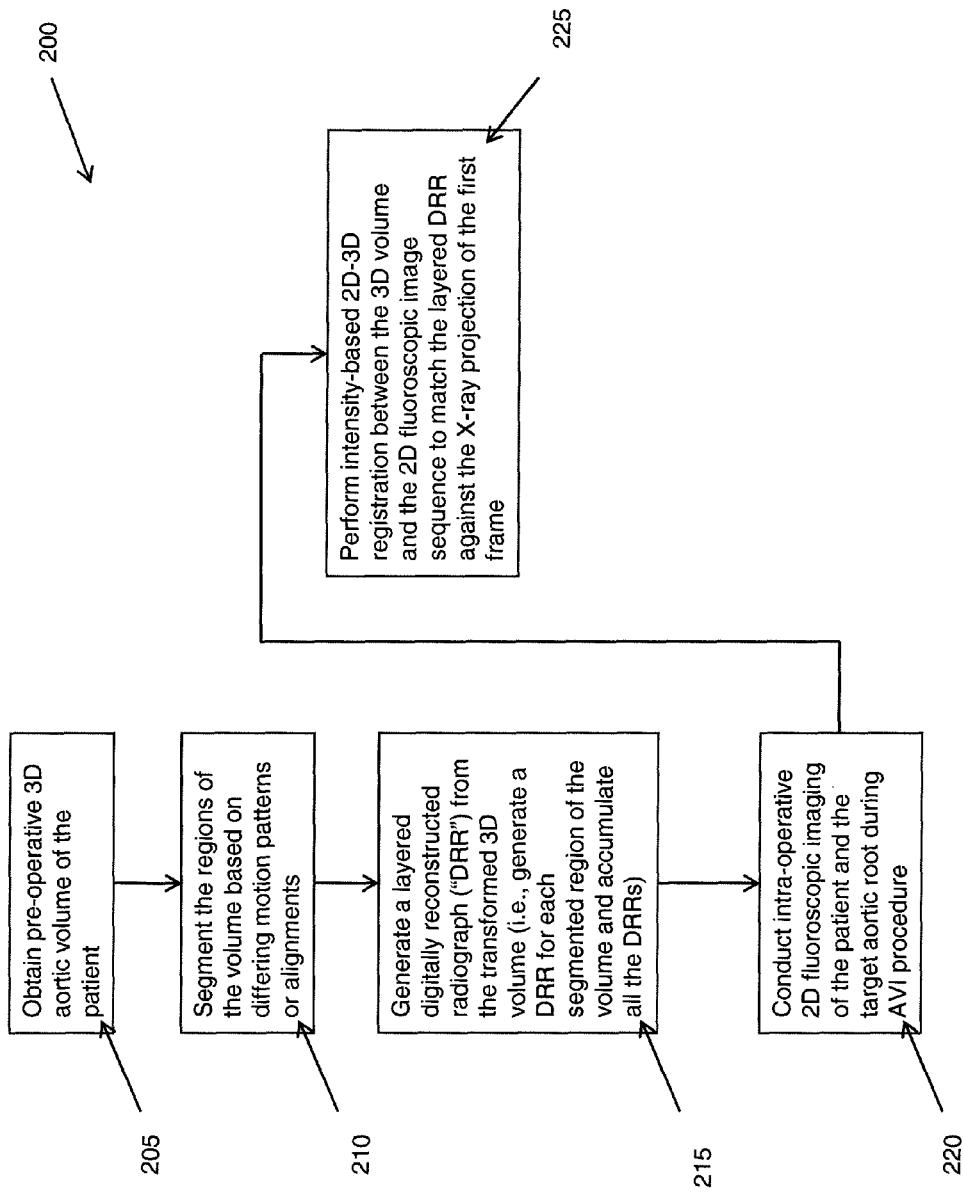
FIG. 3 is a flow chart of a third method to compensate for cardiac and respiratory motion for cardiac imaging carried out in accordance with the present invention.

FIG. 3 shows a third method 200 to compensate for cardiac and respiratory motion in cardiac imaging during minimal invasive (e.g., trans-catheter) AVI procedures in accordance with the present invention. The method 200 provides a layered 2D-3D registration for motion compensation. The method 200 provides acquiring a pre-operative 3D aortic volume (Step 205) and segmenting the regions of the 3D volume based on differing motion patterns or alignments among the regions (Step 210). The method 200 assumes that, after the acquisition of the 3D pre-operative aortic volume, there are various regions within the 3D volume which can be roughly identified through a segmentation process (examples could be regions including calcifications, various sections of the contrasted chambers, etc). These regions are identified based on having different motion patterns or different alignments (rigid body or affine). If the volume is denoted by CT, the sub-volumes (or segmented regions/parts) may be denoted as $CT^i$ such that $CT = U_i{}^i CT$.

After the acquisition of 2D intra-operative X-ray projection sequence (Step 220), the method 200 performs intensity-based 2D-3D registration between the 3D volume and the 2D fluoroscopic image sequence, where the digitally reconstructed radiographs ("DRRs") are generated from the transformed 3D volume and used to match against the X-ray projections (Step 225). Unlike current state of the art methods of intensity-based 2D-3D registration, the method 200 generates layered DRRs from the transformed 3D volume, i.e., generates a DRR for each segmented region of the volume and accumulates all the DRRs for a final layered DRR (Step 215). In particular, each 3D region segmented from the 3D volume would undergo a different transformation (rigid or affine) prior to the DRR generation process, as follows:

$$DRR_i = P(^i CT(T_i)).$$

where $DRR_i$ is a generated digitally reconstructed radiograph for the $i^{th}$ segmented part; P is the projection for generating a $DRR_i$ image; and $T_i$ is a different transformation for each respective $i^{th}$ segmented part. The final DRR is then computed by accumulating these layers of DRR:

$$DRR = \Sigma_i DRR_i.$$

The overall optimization (i.e., registration and tracking) is formulated as a search for a set of transformations, where as the result, the final DRR matches the X-ray projection of a respective frame of the image sequence:

$$\{T_i\} = \arg\max S(^i CT(T_i), \text{Xray}),$$

where S is a similarity measure comparing the DRRs and the X-ray projection images. Conventionally, a transformation to be optimized is just one six degree transformation T (three degrees for translation and three degrees for rotation). In the inventive method 200, the transformation to be optimized is a set of six degree transformations $T_i$ (i=1 . . . n) for the n segmented parts. It is noted that there could be a constraint on the correlation/smoothness among the set of transformations. Also, the optimization can be done efficiently, if the transformations are incrementally updated in the case of tracking and motion complementation of various layers.

Other modifications are possible within the scope of the invention. For example, the subject patient to be scanned may be an animal subject or any other suitable object instead of a human patient. Also, although the steps of each method have been described in a specific sequence, the order of the steps may be re-ordered in part or in whole. Further, although in the described methods the medical professional may use self-contained imaging instrumentation and tools, the medical professional may use other instrumentation or tools in combination with or in place of the imaging instrumentation and tools described for any step or all the steps of the methods, including those that may be made available via telecommunication means. Further, the described methods, or any of their steps, may be carried out automatically by appropriate imaging instrumentation and tools or with some or minimal manual intervention.

What is claimed is:

1. A computer-implemented method of motion compensation in a cardiac imaging using a dynamic overlay of a 3D aortic volume with an intra-operative fluoroscopic image sequence of a target cardiac region, comprising
estimating the motion of the target cardiac region by tracking an image object, located at a relatively fixed position in the target cardiac region and moving in a correlated manner with the motion of the target cardiac region, throughout the image sequence;
describing the correlated motion of the image object with the motion of the target cardiac region by a correlation motion model; and
adjusting the 3D aortic volume in the overlay with the fluoroscopic image sequence using the estimated motion of the target cardiac region and the correlation motion model of the image object with the motion of the target cardiac region,
wherein the fluoroscopic image sequence of the target cardiac region comprises a biplane fluoroscopic image sequence,
wherein the estimating step comprises estimating either or both translational and rigid-body transformation of the target cardiac region by tracking the image object in a 3D space against two views of the biplane fluoroscopic image sequence, and
wherein the two views of the biplane fluoroscopic image sequence are two synchronized biplane views in a synchronized cardiac movement.

2. The method of claim 1, wherein the image object comprises a calcification at the target cardiac region.

3. The method of claim 1, wherein the image object comprises a pigtail catheter at the target cardiac region that injects contrast agent for the fluoroscopic image sequence.

4. The method of claim 1, wherein the image object moves infrequently relative to the target cardiac region in an image plane; moves due to cardiac and respiratory motion; and moves with the target cardiac region motion.

5. The method of claim 1, wherein the cardiac imaging is conducted during a trans-catheter aortic valve implantation (AVI) procedure and the target cardiac region comprises an aortic root.

6. The method of claim 1, wherein the adjusting step comprises adjusting the 3D aortic volume in the 3D space using the estimated transformation.

7. A computer-implemented method for compensating motion in a cardiac imaging, comprising:

overlaying a 3D aortic volume of a patient with two synchronized biplane views of a first frame of a fluoroscopic image sequence of a target cardiac region using a biplane system;
detecting a calcification at the target cardiac region, the calcification at the target cardiac region moving in a correlated manner with a motion of the target cardiac region;
tracking a motion of the calcification on a subsequent frame of the image sequence;
obtaining a corresponding estimated 2D motion vector;
determining if the tracked calcification is sufficiently close to the target cardiac region to represent the motion of the target cardiac region;
building a correlation motion model between the motion of the tracked calcification and the motion of the target cardiac region if the tracked calcification is not sufficiently close to the target cardiac region to represent the motion of the target cardiac region; and
moving the 3D aortic volume in an imaging plane using the estimated 2D motion vector and the correlation motion model,
where the detecting step comprises:
detecting the calcification on the 3D aortic volume;
projecting the detected calcification onto a 2D projection plane using a known geometry; and
detecting the calcification on the fluoroscopic image sequence using the projection as an initial position followed by a local search of dark objects around a neighborhood.

8. The method of claim 7, wherein the overlaying step further comprises confirming an accuracy of the overlay of the 3D aortic volume using a contrast agent injection.

9. The method of claim 7, wherein the detecting step is accomplished by an imaging system automatically or with manual interaction.

10. The method of claim 7, wherein the building step comprises placing a pigtail catheter of a contrast agent injector temporarily stationary at the target cardiac region; tracking in 2D simultaneously the pigtail catheter and the calcification; and correlating the motion of the pigtail catheter with the motion estimated at the tracked calcification.

11. The method of claim 7, wherein the building step comprises obtaining the motion of the target cardiac region by injecting contrast agent and tracking the contrasted target cardiac region.

12. The method of claim 7, wherein the building step comprises obtaining the motion of the target cardiac region by a non-image based localization method.

13. The method of claim 7, wherein the building step comprises building the correlation motion model between the motion of the tracked calcification and the motion of the target cardiac region separately for each cardiac phase.

14. The method of claim 7, wherein the cardiac imaging is conducted during a trans-catheter aortic valve implantation (AVI) procedure and the target cardiac region comprises an aortic root.

15. The method of claim 14, wherein the detecting step comprises detecting the calcification at either or both the aortic root and proximal end of coronary arteries.

16. A computer-implemented method of 3D motion estimation and compensation in a cardiac imaging, comprising:
building a 3D respiratory motion trajectory for each cardiac phase of a patient from a first frame and a subsequent frame of fluoroscopic image sequences of a target cardiac region acquired using a monoplane system during free breathing;

overlaying a 3D aortic volume of the patient with two synchronized biplane views of the first frame of the fluoroscopic image sequences using a biplane system;

detecting a calcification in the target cardiac region;

tracking the calcification on the subsequent frame of the fluoroscopic image sequences;

obtaining an estimated 3D motion vector by intersecting a backprojection ray from the tracked calcification with the respiratory motion trajectory for a current cardiac phase; and moving the 3D aortic volume in 3D using the estimated 3D motion vector.

17. A computer-implemented method for compensating for motion in cardiac imaging, comprising:

overlaying a 3D aortic volume of a patient with two synchronized biplane views of a first frame of a fluoroscopic image sequence of a target cardiac region using a biplane system;

detecting on the both views a pigtail catheter of a contrast agent injector located at a relatively fixed position at the target cardiac region;

reconstructing the pigtail catheter in 3D;

tracking the pigtail catheter in the 3D so that a projection of the pigtail catheter in the 3D overlays best with the pigtail catheter in two synchronized biplane views of a subsequent frame of a fluoroscopic image sequence of the target cardiac region using the biplane system;

obtaining corresponding estimated translational and/or rigid-body transformation;

building a correlation motion model between motions at different parts of the aorta; and moving the 3D aortic volume in the 3D using the estimated translational and/or rigid-body transformation and the correlation motion model.

18. The method of claim 17, wherein the overlaying step further comprises confirming an accuracy of the overlay of the 3D aortic volume with the both views using a contrast agent injection.

19. The method of claim 17, wherein the detecting step is accomplished by an imaging system automatically or with manual interaction.

20. The method of claim 17, wherein the reconstructing step comprises reconstructing the pigtail catheter in 3D from the two pigtail catheter biplane projections.

21. The method of claim 17, wherein the cardiac imaging is conducted during a trans-catheter aortic valve implantation (AVI) procedure and the target cardiac region comprises the aortic root.

22. The method of claim 17, wherein the building step comprises placing the pigtail catheter of the contrast agent injector temporarily at the target cardiac region; and 3D tracking of the pigtail catheter.

23. The method of claim 17, wherein the building step comprises isolating a cardiac motion and building a respiratory motion model.

24. A computer-implemented method for compensating for motion in a cardiac imaging, comprising:

segmenting regions of a 3D aortic volume of a patient;

generating layered digitally reconstructed radiographs (DRRs) for each of the segmented regions of the 3D aortic volume of the patient;

accumulating the layered DRRs from each of the segmented regions to obtain a layered DRR;

performing intensity-based 2D-3D registration between the 3D aortic volume and a 2D fluoroscopic image sequence of a target cardiac region to match the layered DRR against X-ray projections of the image sequence; and adjusting a placement of a representation of the 3D aortic volume in a fluoroscopic imaging plane using results of the 2D-3D registration; and transforming the segmented 3D aortic volume prior to generating the layered DRRs, wherein the transforming is performed by either a rigid or affine transformation for each of the segmented regions of the 3D aortic volume in accordance with the following:

$$DRR_i = P(^iCT(T_i)),$$

where $DRR_i$ is a generated digitally reconstructed radiograph for a $i^{th}$ segmented region; P is a projection for generating the $DRR_i$ image; CT is the 3D aortic volume; and $T_i$ is a different transformation for the respective $i^{th}$ segmented region.

25. The method of claim 24, further comprising segmenting the regions of the 3D aortic volume based on differing motion patterns or alignments among the regions.

26. The method of claim 24, wherein the performing intensity-based 2D-3D registration step matches the layered DRR with the X-ray projections of the image sequence in accordance with the following:

$$\{T_i\} = \arg\max S(P(^iCT(T_i),\text{Xray}),$$

where S is a similarity measure comparing the DRRs and the X-ray projections of the image sequence.

27. The method of claim 24, wherein the cardiac imaging is conducted during a trans-catheter aortic valve implantation (AVI) procedure and the target cardiac region comprises an aortic root.

* * * * *